US012479116B2

(12) United States Patent
O'Neill

(10) Patent No.: US 12,479,116 B2
(45) Date of Patent: Nov. 25, 2025

(54) TRIMMING KNIFE

(71) Applicant: Cancer Diagnostics, Inc., Durham, NC (US)

(72) Inventor: Patrick O'Neill, Durham, NC (US)

(73) Assignee: Cancer Diagnostics, Inc., Durham, NC (US)

( * ) Notice: Subject to any disclaimer, the term of this patent is extended or adjusted under 35 U.S.C. 154(b) by 0 days.

(21) Appl. No.: 18/658,181

(22) Filed: May 8, 2024

(65) Prior Publication Data

US 2024/0375302 A1 Nov. 14, 2024

Related U.S. Application Data

(63) Continuation of application No. 17/510,076, filed on Oct. 25, 2021, now Pat. No. 12,005,597.

(60) Provisional application No. 63/105,590, filed on Oct. 26, 2020.

(51) Int. Cl.

| | |
|---|---|
| ***B26B 5/00*** | (2006.01) |
| ***A61B 10/02*** | (2006.01) |
| ***B25G 1/10*** | (2006.01) |
| ***B25G 3/26*** | (2006.01) |
| ***B26B 29/02*** | (2006.01) |

(52) U.S. Cl.

CPC .................. *B26B 5/00* (2013.01); *B25G 3/26* (2013.01); *B26B 29/02* (2013.01); *A61B 10/0233* (2013.01); *B25G 1/102* (2013.01)

(58) Field of Classification Search

None

See application file for complete search history.

(56) References Cited

U.S. PATENT DOCUMENTS

| | | | |
|---|---|---|---|
| 472,006 | A | 3/1892 | Walker |
| 1,090,398 | A | 3/1914 | Humeston |
| 1,307,717 | A | 6/1919 | Weder, Sr. |
| 1,596,277 | A | 8/1926 | Langbein |
| 1,625,778 | A | 4/1927 | Nickerson |
| 1,706,251 | A | 3/1929 | Edmund |
| 1,813,498 | A | 7/1931 | Kosunen |
| 1,813,723 | A | 7/1931 | Beaver |
| 1,940,855 | A | 12/1933 | Friedman |
| 1,998,188 | A | 4/1935 | Dunn |
| 2,134,973 | A | 11/1938 | Harwell |
| 2,439,071 | A | 4/1948 | Basham |
| 2,793,435 | A | 5/1957 | Donato |
| 5,133,133 | A | 7/1992 | Chiba |
| D743,236 | S | 11/2015 | Fischer |

(Continued)

FOREIGN PATENT DOCUMENTS

| | | | | |
|---|---|---|---|---|
| CN | 206201019 | U | | 5/2017 |
| GB | 158044 | A | * | 1/1921 |
| WO | 2015173823 | | | 11/2015 |

*Primary Examiner* — Hwei-Siu C Payer

(74) *Attorney, Agent, or Firm* — Fitch, Even, Tabin & Flannery LLP

(57) ABSTRACT

In one aspect, a trimming knife is provided that includes a blade and a handle. The blade has a straight leading edge, a straight trailing edge, a straight lower cutting edge, and squared leading and trailing corners between the straight leading and trailing edges and the straight lower cutting edge. The handle includes a gripping portion, a spine to receive the blade, and a blade guard configured to protect the squared trailing corner of the blade with the blade received in the spine.

23 Claims, 4 Drawing Sheets

(56) References Cited

U.S. PATENT DOCUMENTS

| | | | | |
|---|---|---|---|---|
| D867,098 | S | 11/2019 | Patterson | |
| 12,005,597 | B2 * | 6/2024 | O'Neill | B26B 5/00 |
| 2005/0252010 | A1 | 11/2005 | Freeman | |
| 2012/0116432 | A1 | 5/2012 | Orrock | |
| 2014/0345147 | A1 | 11/2014 | Frazer | |
| 2017/0151682 | A1 | 6/2017 | Cheng | |
| 2017/0348863 | A1 | 12/2017 | Kommer | |
| 2020/0276723 | A1 | 9/2020 | Patterson | |
| 2022/0126464 | A1 | 4/2022 | O'Neill | |
| 2024/0375302 | A1 * | 11/2024 | O'Neill | B26B 5/00 |

* cited by examiner

TRIMMING KNIFE

CROSS-REFERENCE TO RELATED APPLICATION(S)

This application is a continuation of U.S. application Ser. No. 17/510,076, filed Oct. 25, 2021, which issued as U.S. Pat. No. 12,005,597 on Jun. 11, 2024, which claims the benefit of U.S. Provisional Application No. 63/105,590, filed Oct. 26, 2020, both of which are incorporated herein by reference in their entireties.

TECHNICAL FIELD

This disclosure relates generally to knives, and more particularly, to trimming knives for use in specimen processing.

BACKGROUND

Trimming knives and blades are well-known in the art for their use in cutting and dissecting tissue in specimen processing, such as pathological and/or histological applications. Such trimming knives are particularly useful for performing biopsies on tissue to determine, for example, if certain tissue is cancerous or to assess other potentially problematic conditions. To perform a biopsy, trimming knives may typically be used for "grossing" tissue, which refers to the examination and dissection of surgical specimens along with preparation of those specimens for additional processing. Known trimming knives typically utilize removable blades that may be disposed of after performing a biopsy or other cutting procedure.

The blades often used in connection with known trimming knives are typically of a rectangular shape including straight leading and trailing edges and a straight lower cutting edge extending between the leading and trailing edges. The trailing edge is toward the handle of the knife and the leading edge is opposite the trailing edge. The blade has squared leading and trailing corners forming junctures between the leading and trailing edges and the straight lower edge. The squared leading and trailing corners can inadvertently catch or drag through a specimen that is being cut. For example, during a backward stroke of the trimming knife when the trimming knife is moving in a rearward direction toward the user, the trailing corner of the blade may accidentally catch on the specimen.

DETAILED DESCRIPTION

In one aspect of the present disclosure, a trimming knife is provided that includes a handle configured to be releasably coupled to a blade. In one embodiment, the blade is a conventional rectangular blade having a straight leading edge, a straight trailing edge, a straight lower cutting edge, and squared leading and trailing corners forming junctures between the leading and trailing edges and the lower cutting edge.

The handle may include a handle for a user to grip during a cutting operation, a spine connected to the handle that is configured to receive at least a portion of the blade, and a blade guard configured to protect the trailing edge corner of the blade. In one embodiment, the blade guard includes an insert that is connected to the handle and has an edge that provides a transition between the lower cutting edge of the blade and a portion of the handle. The edge of the insert may include, for example, a straight and/or curved edge. So configured, during a backward stroke of the trimming knife, the insert may inhibit the trailing corner of the blade from catching on the specimen by contacting and guiding the specimen down around the insert to the lower cutting edge of the blade. In another embodiment, the blade guard may be a portion of the handle. The handle, including a gripping portion and the blade guard, may have a unitary, one-piece construction.

In yet another aspect, a method of assembling a trimming knife is provided including connecting a blade guard of a handle of the trimming knife to a handle of the handle. The connecting may include coupling the blade guard to a spine of the handle and connecting the coupled blade guard and the spine to the handle. The method further includes connecting a blade to the spine, such as sliding the spine onto the blade, and positioning a trailing corner of the blade adjacent the blade guard, such as contacting the blade guard or being spaced by a small gap from the blade guard. In one embodiment, connecting the blade to the handle includes using a fastener. The blade may be removed from the handle after a cutting procedure for disposal thereof by loosening the fastener and sliding the blade out of the spine.

Figure 1:
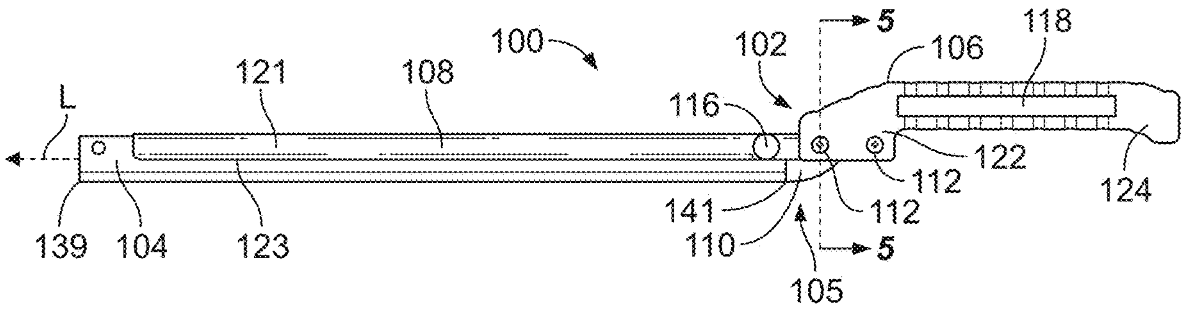
FIG. 1 is a side elevational view of an example trimming knife showing a blade having a squared trailing corner, a handle, and an insert having a curved transition edge.

Referring now to the drawings, and more particularly FIG. 1, an example trimming knife 100 is illustrated including a handle 102 and a blade 104 that may be releasably coupled thereto for use in a cutting procedure. The trimming knife 100 includes a blade guard 105 that may, in one embodiment, include a portion of an insert 110. As shown, the handle 102 includes a handle body 106, a retaining spine 108, and the insert 110 that are coupled together via fasteners 112. The fasteners 112 may include, for example, a screw, a bolt, and/or a pin as some examples. The spine 108 is configured to extend outward from the handle body 106 in a longitudinal direction L and includes a channel 114 (see FIGS. 2 and 5) that is configured to receive an upper portion 145 of the blade 104.

As described in further detail below, the blade 104 may be releasably coupled to the handle 102 by sliding or inserting the upper portion 145 of the blade 104 into and along the channel 114 of the spine 108 until an opening 146 of the blade 104 is aligned with an opening 136 of the spine 108. Then, a retaining member such as a fastener is used to extend through the opening 146 of the blade 104 and keep the blade 104 in the spine 108. In one embodiment, the retaining member includes a thumb screw 116 having a head portion 117 and a shank portion 119, may be used to selectively couple the blade 104 to the spine 108 by inserting the shank portion 119 of the thumb screw 116 through the corresponding, aligned apertures 136, 146 of the spine 108 and the blade 104, respectively.

Once the blade 104 has been coupled to the handle 102, the trimming knife 100 may be used for in various cutting procedures. For example, the trimming knife 100 may be useful for cutting and dissecting tissue specimens taken from patients in medical laboratories for anatomical pathology or histology applications, including but not limited to grossing, sectioning, medical research, and post-mortem examination of patients.

Figure 2:
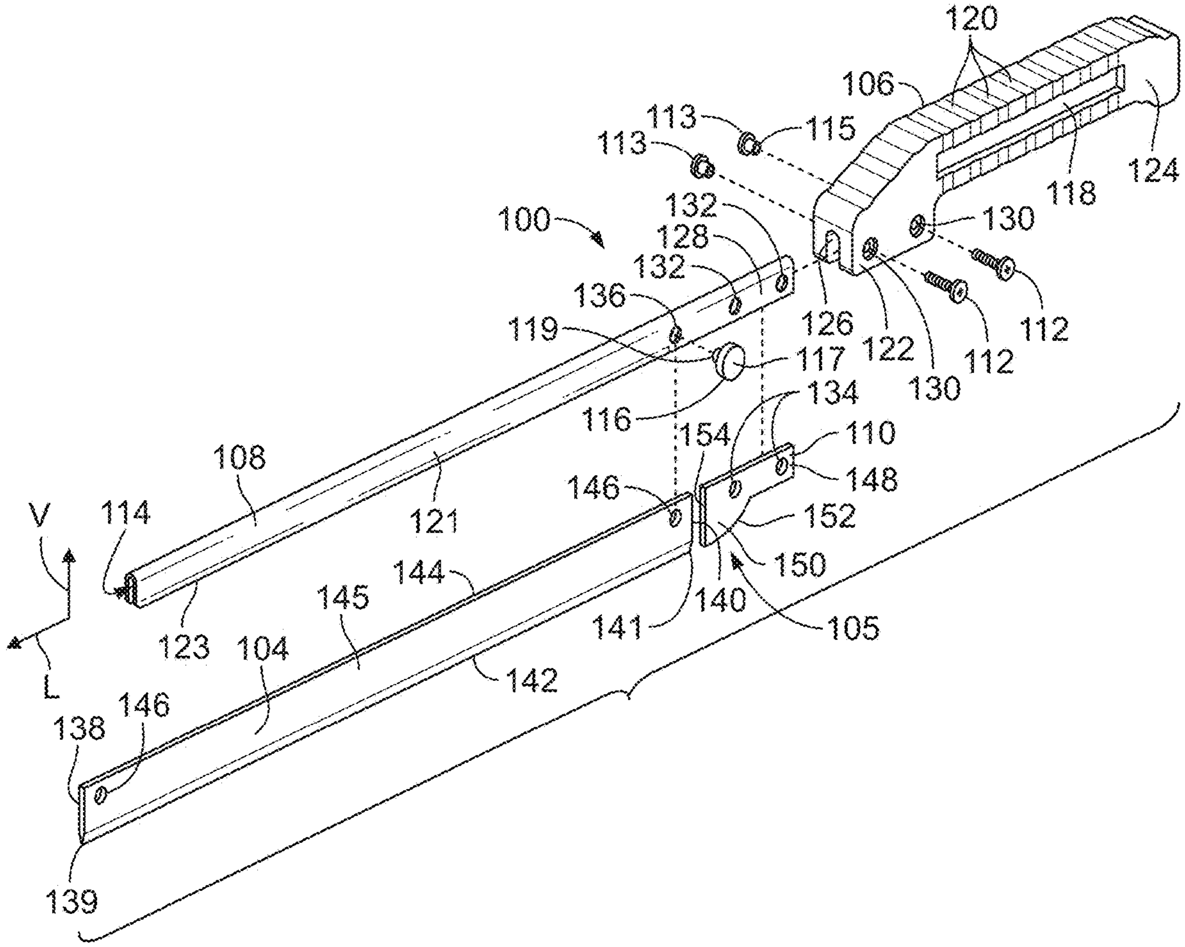
FIG. 2 is a perspective, exploded view of the trimming knife of FIG. 1 showing the handle, a spine, the insert, and the blade.

Referring now to FIG. 2, an exploded view of the trimming knife 100 is shown illustrating the various disassembled components of the handle 102 and the blade 104 detached therefrom. In one aspect, the handle body 106 includes a gripping portion 118 that is adapted to be grasped by a user's hand. As shown, the gripping portion 118 includes a plurality of laterally extending recesses 120 configured to facilitate gripping of the gripping portion 118. In other forms, the gripping portion 118 may include various ridges, depressions, contours, or other textured surfaces either alone or in combination that may promote an improved grip for the user while using the trimming knife 100. In still other forms, the gripping portion 118 may be smooth or may alternatively include a rubber insert or the like to facilitate an improved grip. The handle body 106 may be made of any material with the strength and durability to be used in the cutting procedures described herein, such as a molded plastic material.

The handle body 106 of the handle 102 may also be formed having various different shaped profiles. For example, as illustrated, the gripping portion 118 of the handle body 106 is offset from and at least partially superior to distal and proximal portions 122, 124 of the handle body 106 to provide an ergonomic grip for a user.

As shown in FIGS. 1 and 2, the distal portion 122 of the handle body 106 includes an opening 126 that is sized to receive a proximal portion 128 of the spine 108 therein. In addition, the distal portion 122 of the handle body 106 may include one or more apertures or through-holes 130 on each side of the handle body 106 that extend through the handle body 106 and open into the opening 126. The apertures 130 of the handle body 106 may be configured to receive either a fastener 112 such as a screw, bolt, rivet, or pin, as some examples, or may also receive a securing member on an opposite side of the handle body 106 configured to mate with the fastener 112 and secure the fastener 112 thereto. In some forms, the securing member may be in the form of a post 113 having a threaded bore 115 that is configured to engage a threaded shank of the fastener 112.

The one or more apertures 130 of the handle body 106 are configured to be aligned with one or more apertures 132 of the spine 108 and one or more apertures 134 of the insert 110, respectively, when the spine 108 and insert 110 are assembled with the handle body 106. To assembly the handle 102, a portion of the insert 110 may be positioned in the channel 114 of the spine 108, and the proximal portion 128 of the spine 108 may be received in the opening 126 of the handle body 106 such that the apertures 130, 132, and 134 are aligned. A securing member in the form of post 113 may be positioned proximate the apertures 130 on one side of the handle body 106 and the fasteners 112 may be inserted in the apertures 130 on the opposing side of the handle body 106 such that the fasteners 112 may advance through each of the apertures 130, 132, and 134 and may be coupled to the securing member on the opposite side of the handle body 106 via, for example, the threaded bore 115.

In other forms, the insert 110 may be directly coupled to the handle body 106. In still further forms, the blade guard 105 may be integral with the spine 108. In some embodiments, the handle body 106, spine 108, and the insert 110 may be coupled to one other in alternative forms using, for example, clips, biased locking mechanisms, or the like.

In the illustrated embodiment, the spine 108 is formed as an elongate member having a channel 114 formed therein for receiving at least a portion of the blade 104 and at least a portion of the insert 110. The spine 108 includes sidewalls 121 each having inferior edges 123 that generally converge toward one another such that the edges 123 may be positioned closely adjacent to or contacting side surfaces of the blade 104. The spine 108 may be formed, for example, by folding a strip of rigid material such as metal in half to form sidewalls 121 that define an elongate channel therebetween, such as channel 114, that opens along a length thereof to receive and retain the upper portion 145 of the blade 104 and the insert 110 in a sheath-like manner. So configured, the edges 123 of the sidewalls 121 converge towards the sides of the blade 104 and may engage side surfaces of the blade 104 to facilitate retention of the blade 104 on the handle 102. In some forms, the spine 108 may be formed of a molded plastic or other suitable material.

As described above, the spine 108 includes one or more apertures 132 that are configured to correspond and align with the apertures 130 of the handle body 106 and the apertures 134 of the insert 110 for assembling the handle 102. In addition, the spine 108 may include a blade-retaining aperture 136 configured to receive the shank portion 119 of the thumb screw 116 or other fastener therethrough for releasably coupling the blade 104 to the spine 108.

As shown in FIG. 2, the blade 104 is generally rectangular and includes a distal or leading edge 138, a squared leading corner 139, a proximal or trailing edge 140, a squared trailing corner 141, a cutting edge 142 along a lower side of the blade 104, an upper edge 144 along an upper side of the blade 104, and the upper portion 145 configured to be received in the spine 108. The blade 104 further includes one or more apertures 146 for use in coupling the blade 104 to the spine 108. The blade 104 may be releasably coupled to the handle 102 for either single-use or multi-use applications and may be detached from the handle 102 and disposed of in a convenient manner thereafter.

To attach the blade 104 to the handle 102, a user may slide the upper portion 145 including the upper edge 144 of the blade 104 in the channel 114 in a direction opposite the illustrated direction L, or may otherwise position the upper portion 145 of the blade 104 in the channel 114, and align one of the apertures 146 of the blade 104 with the blade-retaining aperture 136 of the spine 108 that is configured to receive the shank portion 119 of the thumb screw 116. The shank portion 119 of the thumb screw 116 may be advanced into the apertures 136, 146 and threadingly engaged with the spine 108 or a nut on an opposite side of the spine 108 from the head portion 117 of the thumb screw 116. The presence of the thumbscrew shank portion 119 in the aperture 136 and the abutting contact of the blade trailing edge 140 against a stop of the insert 110, such as an insert distal edge 154, inhibits the blade 104 from unintentionally disengaging from the spine 108. The blade 104 connected to the handle 102 may then be used during a cutting procedure. Once a user desires to dispose of the blade 104, the thumb screw 116 may be loosened and the blade 104 may be removed from the spine 108 (e.g., the spine 108 is slid relative to the blade 104 in a direction opposite direction L, or the blade 104 is slid relative to the spine 108 in direction L) and safely disposed of.

Alternatively, the blade 104 may be attached to the handle 102 by sliding the channel 114 of the spine 108 onto the upper portion 145 of the blade 104 in the illustrated direction L. The spine 108 may be slid relative to the blade 104 to position the trailing edge 140 of the blade 104 against a seat, such as a distal edge 154 of the insert 110. When the blade trailing edge 140 is seated against the insert distal edge 154, one of the apertures 146 of the blade 104 is aligned with the blade-retaining aperture 136 of the spine 108, and the thumb screw 116 may then be inserted through apertures 136 and 146 so as to selectively secure the blade 104 in the manner described above.

The blade 104 may be metal, such as stainless steel, or may be formed of other suitable materials for cutting and dissecting tissue specimens. In some forms, the blade 104 may be provided having differing lengths suitable for different types of cutting procedures. For instance, a shorter blade may be desirable for cutting a smaller specimen or portion of tissue during a pathological or histological dissection.

Figure 3:
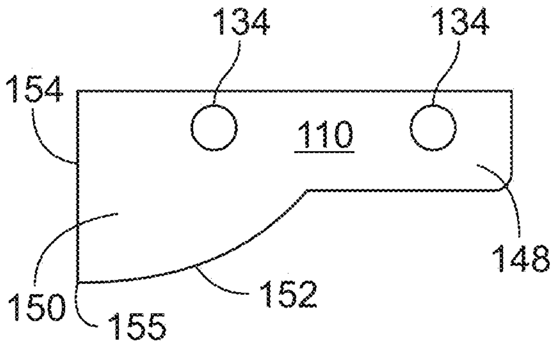
FIG. 3 is a side elevational view of the insert of FIG. 2.

Regarding FIGS. 2 and 3, the insert 110 includes a mounting portion 148 and a blade guard portion 150. The mounting portion 148 may include the one or more apertures 134 and is configured to be at least partially positioned in the channel 114 of the spine 108. As shown in FIG. 3, the blade guard portion 150 of the insert 110 includes an edge 152 that is configured to provide a smooth transition between the lower cutting edge 142 of the blade 104 and the handle body 106. In FIGS. 1-3, the edge 152 is curved. The blade guard portion 150 overlaps a squared, trailing corner 141 of the blade 104 in the longitudinal direction. The blade guard portion 150 may contact the specimen when the blade 104 is moved backwards, toward the user, in a direction opposite direction L (see FIG. 2) rather than the trailing edge corner 141 of the blade 104 when the specimen is adjacent the insert 110. So configured, during a backward stroke of the trimming knife 100 while cutting a specimen, the arcuate edge 152 of the blade guard portion 150 may inhibit the squared trailing corner 141 of the blade 104 from contacting or catching on the specimen being cut.

A distal edge 154 of the insert 110 may be sized such that a height thereof substantially corresponds to a height of the trailing edge 140 of the blade 104. In one embodiment, the squared corner 141 of the trailing edge 140 does not extend below a juncture 155 between the edges 152, 154 of the insert 110. Accordingly, the juncture 155 of the insert 110 is preferably either at an equal height as the trailing edge corner 141 of the blade 104 or slightly below in the vertical direction V. So configured, in an example where the trimming knife 100 is being used to slice a specimen, during a backward stroke (toward the user) the first portion of the trimming knife 100 that could contact the specimen would be the arcuate transition edge 152 of the blade guard portion 150 instead of the trailing corner 141 of the blade 104. Rather than catching on or tearing the specimen if contacted by the trailing corner 141, the edge 152 of the insert 110 may contact the specimen and guide the specimen down around the blade guard portion 150 to the cutting edge 142 of the blade 104.

Figure 4:
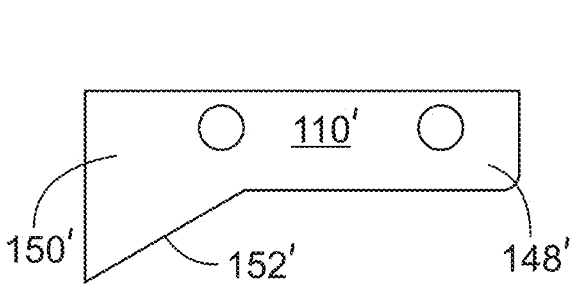
FIG. 4 is a side elevational view of another insert.

The transition edge 152 of the insert 110 may be formed having a variety of different profiles. For example, as shown in FIG. 3, the transition edge 152 may have an arcuate profile such that any portion of specimen or other surface contacted thereby may be guided along the transition edge 152 and below the insert 110 during a backward stroke of the trimming knife 100, as opposed to catching on the trailing corner 141 of the blade 104. In another embodiment, such as shown in FIG. 4, an insert 110' may include a mounting portion 148' and a blade guard portion 150'. The blade guard portion 150' includes an edge 152' having a linear, angled configuration to similarly inhibit an object being trimmed from contacting and catching on the trailing corner 141 of the blade 104. The edge 152' provides a tapered transition between the blade cutting edge 142 and the handle body 106 and directs the object being cut toward the blade cutting edge 142 as the knife is drawn backward toward the user if the object is adjacent the insert 110'.

The blade guard portions described herein may have various shapes provided that the approximate shape of the transition edge increases in height towards the trailing edge 140 of the blade 104 to inhibit the trailing corner 141 of the blade 104 from catching on a specimen or another object being cut with a backward stroke of the knife, and as long as the transition edge extends at the same height or below the trailing edge corner 141 in the vertical direction V. Various embodiments of inserts contemplated herein may be easily exchanged by disassembling the handle 102 and selecting a new insert to include. In some forms, the insert 110 may be a metal material such as stainless steel. In other forms, the insert may be a polymer such as a molded plastic material.

Figure 5:
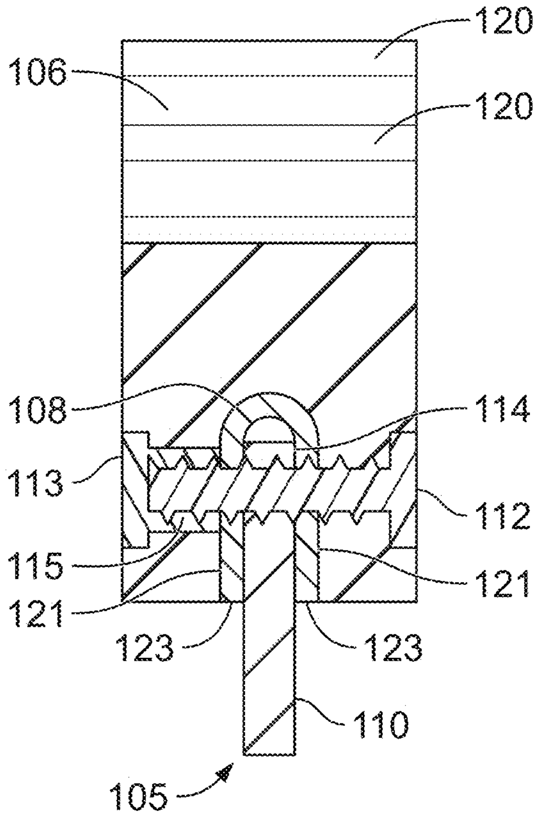
FIG. 5 is a cross-sectional view taken along line 5-5 in FIG. 1 showing the connection between the insert, the spine, and the handle of the trimming knife.

Referring now to FIGS. 2 and 5, an example method of assembling the trimming knife 100 will be described. In an initial step, the blade guard 105 formed as insert 110 may be placed within the channel 114 of the spine 108 such that the apertures 134 of the insert 110 are aligned with the corresponding apertures 132 of the spine 108. The spine 108 and insert 110 may then be received in the opening 126 of the handle body 106 such that the apertures 130 are likewise aligned with the apertures 132, 134. Securing members, such as a post 113 having a threaded bore 115, may be positioned and inserted in the apertures 130, 132, 134 on one side of the handle body 106. Fasteners 112 such as screws may thereafter be inserted through the corresponding sets of apertures 130, 132, 134 on an opposite side of the handle body 106 such that threads of the fasteners 112 may engage the threaded bores 115 of the posts 113 and be releasably attached thereto to couple the handle body 106, spine 108, and insert 110 together in a single handle 102. This coupling is shown in further detail in FIG. 5, showing the insert 110 nested within the channel 114 of the spine 108 and further positioning in the opening 126 of the handle body 106 with fastener 112 extending therethrough.

When the trimming knife 100 is desired for use in a cutting operation, a blade 104 may be selected and at least partially inserted into the channel 114 between the sidewalls 121 of the spine 108. In one approach, the spine 108 may be slid along the blade 104 in direction L (shown in FIG. 2) until the blade trailing edge 140 abuts or is spaced slightly from the insert distal edge 154 and blade-retaining aperture 136 of the spine 108 and the aperture 146 of the blade 104 are aligned and the thumb screw 116 may be advanced through the apertures 136, 146 to secure the blade 104 to the handle 102. In another approach, the spine 108 may be held stationary and the blade 104 slid along the spine 108. As described in further detail above, the insert 110 positioned adjacent the trailing edge 140 of the blade 104 is configured to inhibit the trailing corner 141 from catching or otherwise inadvertently contacting any portion of a specimen being cut. After being used for a cutting procedure, the blade 104 may be removed and disposed of by loosening the thumb screw 116 and removing the blade 104 from the channel 114 of the spine 108.

Figure 6:
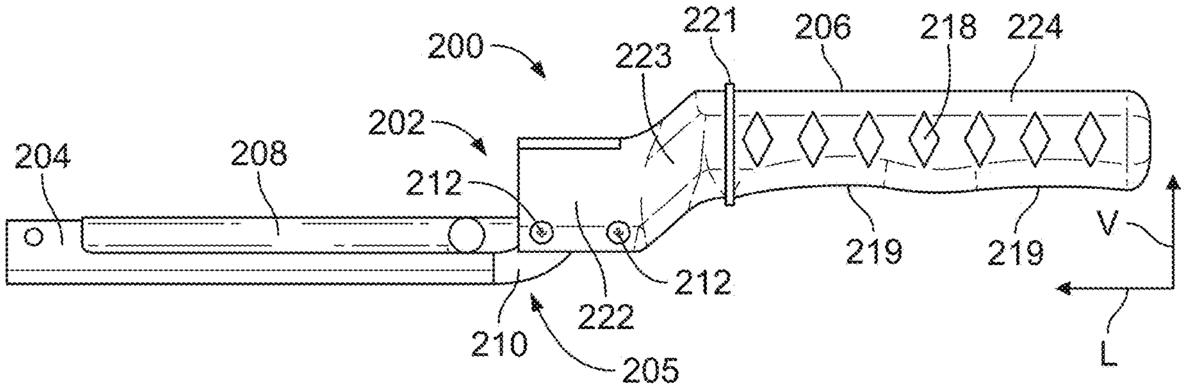
FIG. 6 is a side elevational view of another trimming knife having a handle with a rounded gripping portion.

Referring now to FIG. 6, an alternative trimming knife 200 similar to trimming knife 100 is shown including a handle 202 and a blade 204 that may be releasably coupled thereto. As shown, the handle 202 includes a handle body 206, a retaining spine 208, and a blade guard 205 at least partially including an insert 210 that are coupled together via fasteners 212. The blade 204, spine 208, and insert 210 are substantially similar to the blade 104, spine 108, and insert 110 discussed above such that any differences will be highlighted hereinafter.

As illustrated, the handle body 206 has an ovular cross-section and includes a distal portion 222 and a proximal portion 224. The proximal portion 224 is offset from, and at least partially superior to, the distal portion 222 in the vertical direction V. An intermediate connecting portion 223 may extend between the distal and proximal portions 222, 224, and may be angled relative to the longitudinal direction L to provide the offset described above with respect to the distal and proximal portions 222, 224. The proximal portion 224 includes a gripping portion 218 that is configured to be gripped by a user during use of the trimming knife 200. As shown, the gripping portion 218 includes an undulating lower contour 219 to provide an ergonomic grip by the user and further includes a ridge 221 extending outward of the gripping portion 218 to abut the user's forefinger and help the user accurately grasp the handle 206. In some circumstances, a user may prefer a different shaped handle (such as handle body 106 or another alternative handle) for use in connection with their trimming knife. It should be understood that such handles could be swapped out or exchanged for one another with relative ease by detaching the spine and insert coupled thereto.

Figure 7:
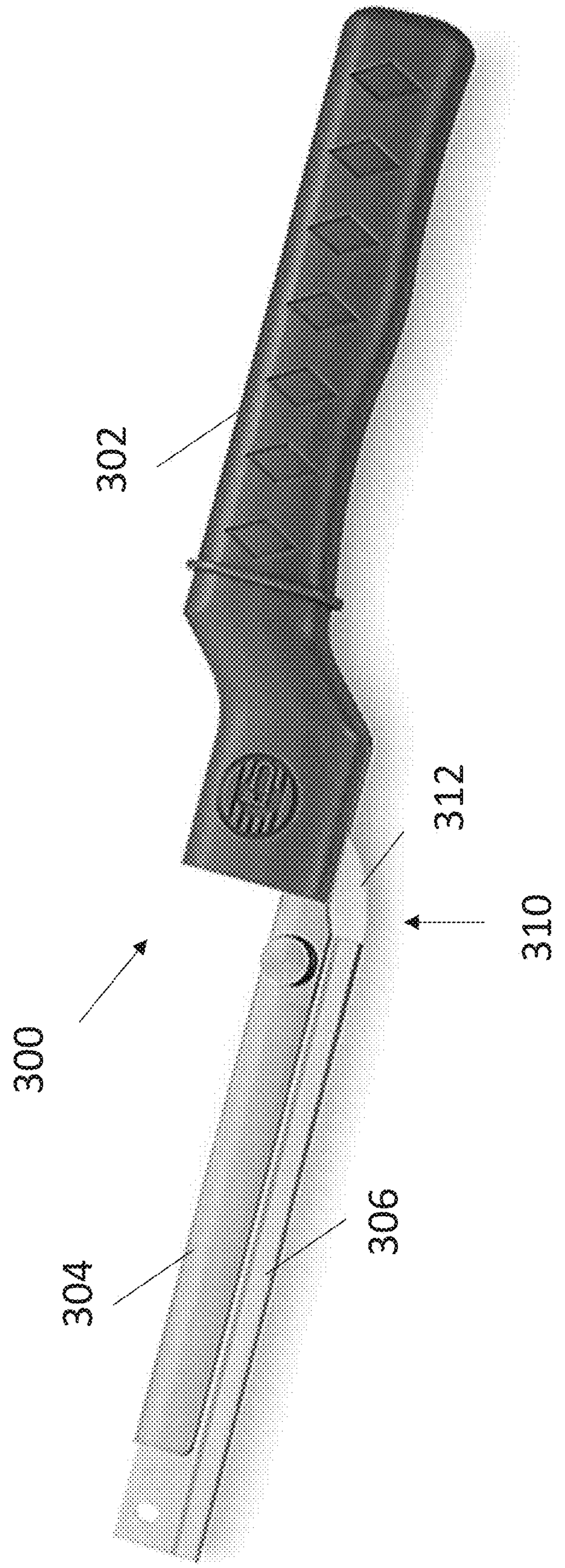
FIG. 7 is a perspective view of another trimming knife.

With reference to FIG. 7, a trimming knife 300 is provided that is similar in many respects to the trimming knife discussed above such that differences will be highlighted. The trimming knife 300 includes a handle 302, a spine 304, a blade 306, and a blade guard 310 including an insert 312. The handle 302 includes a handle body having two halves and pegs that extend through openings of the insert 312 and the spine 304. During assembly of the handle 300, the pegs are inserted through the openings of the insert 312 and spine 304, then the two halves of the handle are secured together about the pegs, insert 312, and spine 304. For example, the two halves of the handle 302 may be made of plastic and the two halves may be secured together using ultrasonic welding.

Uses of singular terms such as "a," and "an," are intended to cover both the singular and the plural, unless otherwise indicated herein or clearly contradicted by context. The terms "comprising," "having," "including," and "containing" are to be construed as open-ended terms. It is intended that the phrase "at least one of" as used herein be interpreted in the disjunctive sense. For example, the phrase "at least one of A and B" is intended to encompass A, B, or both A and B.

While there have been illustrated and described particular embodiments of the present invention, it will be appreciated that numerous changes and modifications will occur to those skilled in the art, and it is intended for the present invention to cover all those changes and modifications which fall within the scope of the appended claims.

The invention claimed is:

1. A trimming knife handle comprising:

a handle body;

an elongate spine connected to the handle body and having a proximal end received in the handle body, the spine having a distal end opposite the proximal end;

a channel of the spine configured to receive an upper portion of a blade;

a seat for a straight trailing edge of the blade spaced distally from the proximal end of the spine for positioning the straight trailing edge of the blade distal of the proximal end of the spine;

a blade guard having a lower portion below the channel of the spine, the lower portion configured to be adjacent a squared trailing corner of the blade when an upper portion of the blade is received in the channel;

wherein the spine has a through opening; and a fastener configured to extend in the through opening of the spine and an opening of the blade for retaining the blade in the channel.

2. The trimming knife handle of claim 1 wherein the lower portion of the blade guard has a lower end configured to be level with a straight lower cutting edge of the blade with when the upper portion of the blade is received in the channel of the spine.

3. The trimming knife handle of claim 1 wherein the lower portion of the blade guard includes a lower corner configured to be level with a straight lower cutting edge of the blade when the upper portion of the blade is received in the channel of the spine.

4. The trimming knife handle of claim 3 wherein the lower corner of the blade guard is below and distal of the proximal end of the spine.

5. The trimming knife handle of claim 1 wherein the blade guard includes a straight edge; and wherein the seat comprises a portion of the straight edge in the channel of the spine; and wherein the lower portion of the blade guard comprises a portion of the straight edge outside of the channel of the spine.

6. The trimming knife handle of claim 1 wherein the fastener comprises a thumbscrew.

7. The trimming knife handle of claim 1 wherein the through opening of the spine is above and distal of the lower portion of the blade guard.

8. The trimming knife handle of claim 1 wherein the lower portion of the blade guard is below and distal of the proximal end of the spine.

9. The trimming knife handle of claim 1 wherein the blade guard comprises an insert connected to the spine, the insert having an upper portion that includes the seat.

10. The trimming knife handle of claim 9 wherein the upper portion of the insert is in the channel of the spine.

11. The trimming knife handle of claim 1 wherein the through opening of the spine includes threads; and wherein the fastener is configured to engage the threads of the through opening and adapted to extend in the opening of the blade for securing the blade in the channel when the upper portion of the blade is received in the channel.

12. The trimming knife handle of claim 1 wherein the spine includes a pair of sidewalls that define at least a portion of the channel;

wherein the through opening of the spine includes a pair of through openings in the sidewalls of the spine; and wherein the fastener comprises a thumbscrew configured to extend through the through openings of the sidewalls and through the opening of the blade to for retaining the blade in the channel when the upper portion of the blade is received in the channel.

13. The trimming knife handle of claim 1 wherein the blade guard has an upper portion that includes the seat.

14. The trimming knife handle of claim 1 wherein the seat is at least partially in the channel.

15. The trimming knife handle of claim 1 wherein the handle body is a plastic material; and wherein the spine is a metallic material.

16. The trimming knife handle of claim 1 wherein the handle body has a recess; and wherein the proximal end of the spine is in the recess.

17. The trimming knife handle of claim 1 wherein the seat and the blade guard comprise portions of a straight edge.

18. A trimming knife handle comprising:

a handle body;

an elongate spine connected to the handle body and having a proximal end received in the handle body, the spine having a distal end opposite the proximal end;

a channel of the spine configured to receive an upper portion of a blade;

a seat for a straight trailing edge of the blade spaced distally from the proximal end of the spine for positioning the straight trailing edge of the blade distal of the proximal end of the spine;

a blade guard having a lower portion below the channel of the spine, the lower portion configured to be adjacent a squared trailing corner of the blade when an upper portion of the blade is received in the channel;

wherein the spine has a unitary, one-piece construction and includes a pair of sidewalls and a connecting portion connecting the sidewalls, wherein the sidewalls and the connecting portion define at least a portion of the channel; and wherein the connecting portion extends uninterrupted from the proximal end to the distal end of the spine.

19. A trimming knife comprising:

a blade having an upper portion, a straight trailing edge, a straight lower cutting edge, and a squared trailing corner, wherein the straight trailing edge and the straight lower cutting edge of the blade meet at the squared trailing corner of the blade;

a handle body;

an elongate spine connected to the handle body and having a proximal end received in the handle body, the spine having a distal end opposite the proximal end;

a channel of the spine configured to receive the upper portion of the blade;

a seat for the straight trailing edge of the blade spaced distally from the proximal end of the spine for positioning the straight trailing edge of the blade distal of the proximal end of the spine; and a blade guard having a lower portion below the channel of the spine, the lower portion configured to be adjacent the squared trailing corner of the blade when the upper portion of the blade is received in the channel.

20. The trimming knife of claim 19 wherein the blade has a straight lower cutting edge; and wherein the lower portion of the blade guard has a lower end configured to be level with the straight lower cutting edge of the blade with the upper portion of the blade received in the channel of the spine.

21. The trimming knife of claim 19 wherein the spine includes a through opening;

wherein the upper portion of the blade includes a through opening; and a fastener to extend in the through openings and keep the blade connected to the spine.

22. The trimming knife of claim 19 wherein the seat has an upper portion in the channel of the spine and a lower portion outside of the channel of the spine.

23. The trimming knife of claim 19 wherein the blade has a straight leading edge; and wherein the upper portion of the blade includes a first through opening proximate the straight leading edge and a second through opening proximate the straight trailing edge.

* * * * *